US012527941B2

(12) United States Patent
Howell

(10) Patent No.: US 12,527,941 B2
(45) Date of Patent: Jan. 20, 2026

(54) INTRODUCER COMPONENTS, ASSEMBLIES, AND METHODS THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 658 days.

(21) Appl. No.: 17/884,402

(22) Filed: Aug. 9, 2022

(65) Prior Publication Data

US 2023/0039733 A1 Feb. 9, 2023

Related U.S. Application Data

(60) Provisional application No. 63/231,112, filed on Aug. 9, 2021.

(51) Int. Cl.
*A61M 25/09* (2006.01)
*A61M 5/32* (2006.01)

(52) U.S. Cl.
CPC .... *A61M 25/09041* (2013.01); *A61M 5/3287* (2013.01); *A61M 5/3293* (2013.01)

(58) Field of Classification Search
CPC .......... A61M 5/158; A61M 2005/1581; A61M 25/06; A61M 25/065; A61M 25/09041
See application file for complete search history.

(56) References Cited

U.S. PATENT DOCUMENTS

| | | | |
|---|---|---|---|
| 3,076,457 | A | 2/1963 | Copen |
| 3,359,978 | A | 12/1967 | Smith, Jr. |
| 4,743,265 | A | 5/1988 | Whitehouse et al. |
| 4,886,507 | A | 12/1989 | Patton et al. |

(Continued)

FOREIGN PATENT DOCUMENTS

| | | | |
|---|---|---|---|
| CN | 106422031 | B | 7/2021 |
| DE | 4136051 | A1 | 7/1993 |

(Continued)

OTHER PUBLICATIONS

PCT/US2022/029561 filed May 17, 2022 International Search Report and Written Opinion dated Nov. 9, 2022.

(Continued)

*Primary Examiner* — Laura A Bouchelle
(74) *Attorney, Agent, or Firm* — Rutan & Tucker LLP

(57) ABSTRACT

Disclosed are introducer components, assemblies, and methods. For example, an introducer assembly can include a syringe and a needle assembly fluidly connected thereto. The needle assembly can include a needle and an access guidewire-advancement mechanism mounted on a proximal linear portion of a needle shaft of the needle. The needle shaft can include a sigmoid portion between a distal linear portion of the needle shaft and the proximal linear portion as well as a port in a transition from the sigmoid portion to the distal linear portion of the needle shaft. An access guidewire can be loaded in both the access guidewire-advancement mechanism and a needle-shaft lumen in the distal linear portion of the needle shaft in a ready-to-deploy state of the introducer assembly. In this way, the access guidewire can be immediately advanced into a blood-vessel lumen upon establishing a needle tract thereto with the needle.

24 Claims, 4 Drawing Sheets

(56) References Cited

U.S. PATENT DOCUMENTS

| | | | |
|---|---|---|---|
| 4,935,008 | A | 6/1990 | Lewis, Jr. |
| 4,994,040 | A | 2/1991 | Cameron et al. |
| 5,290,244 | A | 3/1994 | Moonka |
| 5,380,290 | A | 1/1995 | Makower et al. |
| 5,735,813 | A | 4/1998 | Lewis |
| 5,853,391 | A | 12/1998 | Bell |
| 5,971,957 | A | 10/1999 | Luther et al. |
| 6,019,736 | A | 2/2000 | Avellanet et al. |
| 6,159,195 | A | 12/2000 | Ha et al. |
| 7,172,587 | B2 | 2/2007 | Poole et al. |
| 7,938,820 | B2 * | 5/2011 | Webster ................ A61M 25/10 604/528 |
| 8,882,713 | B1 | 11/2014 | Call et al. |
| 2002/0072712 | A1 | 6/2002 | Nool et al. |
| 2003/0205843 | A1 | 11/2003 | Adams |
| 2004/0092879 | A1 | 5/2004 | Kraus et al. |
| 2004/0236346 | A1 | 11/2004 | Parker |
| 2005/0021124 | A1 | 1/2005 | Cunniffe et al. |
| 2005/0043684 | A1 | 2/2005 | Basta et al. |
| 2007/0276288 | A1 | 11/2007 | Khaw |
| 2008/0009793 | A1 | 1/2008 | Dabbs |
| 2008/0027380 | A1 | 1/2008 | Wholey et al. |
| 2008/0091137 | A1 | 4/2008 | Reavill |
| 2009/0187147 | A1 | 7/2009 | Kurth et al. |
| 2011/0071502 | A1 | 3/2011 | Asai |
| 2013/0184659 | A1 | 7/2013 | Byrnes et al. |
| 2015/0224287 | A1 | 8/2015 | Bian et al. |
| 2015/0320968 | A1 | 11/2015 | Konstantino et al. |
| 2016/0175563 | A1 | 6/2016 | Woehr et al. |
| 2016/0220786 | A1 | 8/2016 | Mitchell et al. |
| 2016/0310704 | A1 | 10/2016 | Ng et al. |
| 2017/0035996 | A1 | 2/2017 | O'Fallon |
| 2017/0258489 | A1 | 9/2017 | Galili et al. |
| 2017/0296792 | A1 | 10/2017 | Ornelas Vargas et al. |
| 2018/0043138 | A1 | 2/2018 | Chu |
| 2019/0015637 | A1 | 1/2019 | Jacobs |
| 2019/0022353 | A1 | 1/2019 | Khanicheh et al. |
| 2019/0038113 | A1 | 2/2019 | Chu |
| 2019/0134374 | A1 | 5/2019 | Korkuch et al. |
| 2020/0008838 | A1 | 1/2020 | Frey et al. |
| 2020/0107859 | A1 | 4/2020 | Zhu |
| 2020/0147349 | A1 | 5/2020 | Holt |
| 2020/0170559 | A1 | 6/2020 | Burkholz et al. |
| 2020/0188650 | A1 | 6/2020 | Al-Ali |
| 2020/0197682 | A1 | 6/2020 | Franklin et al. |
| 2021/0085927 | A1 | 3/2021 | Howell |
| 2021/0121661 | A1 | 4/2021 | Howell |
| 2021/0330941 | A1 | 10/2021 | Howell et al. |
| 2021/0332274 | A1 | 10/2021 | Hoshi et al. |
| 2021/0361915 | A1 | 11/2021 | Howell et al. |
| 2021/0402153 | A1 | 12/2021 | Howell et al. |
| 2022/0362524 | A1 | 11/2022 | Howell |
| 2022/0370762 | A1 | 11/2022 | Blanchard et al. |
| 2023/0041261 | A1 | 2/2023 | Howell |
| 2023/0043989 | A1 | 2/2023 | Howell |
| 2023/0064542 | A1 | 3/2023 | Howell |
| 2023/0086639 | A1 | 3/2023 | Howell |
| 2023/0096377 | A1 | 3/2023 | West et al. |
| 2023/0149667 | A1 | 5/2023 | Lindekugel et al. |
| 2023/0181878 | A1 | 6/2023 | Blanchard et al. |
| 2023/0201537 | A1 | 6/2023 | Howell et al. |
| 2023/0201538 | A1 | 6/2023 | Howell et al. |
| 2023/0218867 | A1 | 7/2023 | Howell et al. |
| 2023/0381481 | A1 | 11/2023 | Pizzato |
| 2024/0082549 | A1 | 3/2024 | Spataro et al. |
| 2024/0226507 | A1 | 7/2024 | Spataro |

FOREIGN PATENT DOCUMENTS

| | | | |
|---|---|---|---|
| DE | 19750090 | A1 | 6/1999 |
| EP | 0067260 | A1 | 12/1982 |
| EP | 0155331 | A1 | 9/1985 |
| EP | 0499147 | A2 | 8/1992 |
| EP | 0641571 | A1 | 3/1995 |
| EP | 1338299 | A1 | 8/2003 |
| EP | 3193813 | A1 | 7/2017 |
| EP | 3473291 | A1 | 4/2019 |
| JP | H02255156 | A | 10/1990 |
| JP | H077971 | Y2 | 3/1995 |
| JP | 2004254879 | A | 9/2004 |
| JP | 2009232917 | A | 10/2009 |
| JP | 5101359 | B2 | 12/2012 |
| WO | 89/06986 | A1 | 8/1989 |
| WO | 95/09662 | A1 | 4/1995 |
| WO | 98/10821 | A1 | 3/1998 |
| WO | 99/59651 | A2 | 11/1999 |
| WO | 02/078776 | A2 | 10/2002 |
| WO | 2005096778 | A2 | 10/2005 |
| WO | 2009094089 | A1 | 7/2009 |
| WO | 2011143621 | A1 | 11/2011 |
| WO | 2012101089 | A1 | 8/2012 |
| WO | 2013064215 | A1 | 5/2013 |
| WO | 2015/061172 | A1 | 4/2015 |
| WO | 2016042544 | A1 | 3/2016 |
| WO | 2016123278 | A1 | 8/2016 |
| WO | 2016187063 | A1 | 11/2016 |
| WO | 2020/206280 | A2 | 10/2020 |
| WO | 2021216902 | A1 | 10/2021 |
| WO | 2021222116 | A2 | 11/2021 |
| WO | 2022/204049 | A1 | 9/2022 |
| WO | 2022/246271 | A2 | 11/2022 |
| WO | 2022/245774 | A3 | 12/2022 |
| WO | 2023014994 | A1 | 2/2023 |
| WO | 2023018669 | A1 | 2/2023 |
| WO | 2023018729 | A1 | 2/2023 |
| WO | 2023018733 | A1 | 2/2023 |
| WO | 2023028138 | A2 | 3/2023 |
| WO | 2023049174 | A1 | 3/2023 |
| WO | 2023091586 | A1 | 5/2023 |
| WO | 2023114324 | A1 | 6/2023 |
| WO | 2023122312 | A1 | 6/2023 |
| WO | 2023129457 | A1 | 7/2023 |
| WO | 2023137077 | A1 | 7/2023 |
| WO | 2024059073 | A1 | 3/2024 |
| WO | 2024151869 | A1 | 7/2024 |

OTHER PUBLICATIONS

PCT/US2022/039742 filed Aug. 8, 2022 International Search Report and Written Opinion dated Dec. 21, 2022.

PCT/US2022/039852 filed Aug. 9, 2022 International Search Report and Written Opinion dated Dec. 6, 2022.

PCT/US2022/039861 filed Aug. 9, 2022, International Search Report and Written Opinion dated Jan. 5, 2023.

PCT/US2022/044242 filed Sep. 21, 2022 International Search Report and Written Opinion dated Feb. 8, 2023.

PCT/US2022/039742 filed Aug. 8, 2022 International Preliminary Report on Patentability dated Feb. 13, 2024.

PCT/US2022/041368 filed Aug. 24, 2022 International Preliminary Report on Patentability dated Feb. 27, 2024.

PCT/US2022/044242 filed Sep. 21, 2022 International Preliminary Report on Patentability dated Mar. 26, 2024.

PCT/US2022/053887 filed Dec. 22, 2022 International Search Report and Written Opinion dated May 8, 2023.

PCT/US2022/030365 filed May 20, 2022 International Search Report and Written Opinion dated Apr. 4, 2023.

PCT/US2022/041368 filed Aug. 24, 2022 International Search Report and Written Opinion dated Mar. 21, 2023.

PCT/US2022/050280 filed Nov. 17, 2022 International Search Report and Written Opinion dated Apr. 17, 2023.

PCT/US2022/052884 filed Dec. 14, 2022 International Search Report and Written Opinion dated May 15, 2023.

PCT/US2022/053724 filed Dec. 21, 2022 International Search Report and Written Opinion dated May 10, 2023.

PCT/US2023/010623 filed Jan. 11, 2023, International Search Report and Written Opinion dated Jul. 6, 2023.

PCT/US2022/021187 filed Mar. 21, 2022 International Search Report and Written Opinion dated Jun. 17, 2022.

PCT/US2023/032545 filed Sep. 12, 2023 International Search Report and Written Opinion dated Feb. 5, 2024.

(56) References Cited

OTHER PUBLICATIONS

U.S. Appl. No. 17/746,113, filed May 17, 2022 Restriction Requirement dated Dec. 11, 2024.
U.S. Appl. No. 17/700,152, filed Mar. 21, 2022 Restriction Requirement dated Jan. 31, 2025.
U.S. Appl. No. 17/746,113, filed May 17, 2022 Non-Final Office Action dated Apr. 7, 2025.
U.S. Appl. No. 17/750,097, filed May 20, 2022 Restriction Requirement dated Mar. 20, 2025.
U.S. Appl. No. 17/884,307, filed Aug. 9, 2022 Non-Final Office Action dated Apr. 2, 2025.
Adam et al. (Gastrointestinal Endoscopy vol. 77, No. 5S 2013, 1020) (Year: 2010).
Lapalu et al. "Totally implantable port management: impact of positive pressure during needle withdrawal on catheter tip occlusion (an experimental study)" The Journal of Vascular Access 2010; 11: 46-51, 2010 Wichtig Editore, Original Article, 2010.
PCT/US2024/011269 filed Jan. 11, 2024 International Search Report and Written Opinion dated May 15, 2024.
U.S. Appl. No. 17/700,152, filed Mar. 21, 2022 Non-Final Office Action dated Aug. 14, 2025.
U.S. Appl. No. 17/700,152, filed Mar. 21, 2022 Restriction Requirement dated Apr. 29, 2025.
U.S. Appl. No. 17/750,097, filed May 20, 2022 Notice of Allowance dated Jun. 27, 2025.
U.S. Appl. No. 17/883,490, filed Aug. 8, 2022 Non-Final Office Action dated Jul. 31, 2025.
U.S. Appl. No. 17/894,759, filed Aug. 24, 2022 Non-Final Office Action dated Jun. 16, 2025.
U.S. Appl. No. 17/949,734, filed Sep. 21, 2022 Non-Final Office Action dated Aug. 4, 2025.
U.S. Appl. No. 18/081,491, filed Dec. 14, 2022 Non-Final Office Action dated Aug. 22, 2025.
PCT/US2025/032881 filed Jun. 9, 2025 International Search Report and Written Opinion dated Sep. 24, 2025.
U.S. Appl. No. 17/884,307, filed Aug. 9, 2022 Final Office Action dated Oct. 23, 2025.
U.S. Appl. No. 17/894,759, filed Aug. 24, 2022 Final Office Action dated Sep. 24, 2025.
U.S. Appl. No. 18/086,517, filed Dec. 21, 2022 Non-Final Office Action dated Oct. 31, 2025.
U.S. Appl. No. 18/087,676, filed Dec. 22, 2022 Restriction Requirement dated Oct. 8, 2025.
U.S. Appl. No. 18/095,968, filed Jan. 11, 2023 Restriction Requirement dated Nov. 24, 2025.

* cited by examiner

INTRODUCER COMPONENTS, ASSEMBLIES, AND METHODS THEREOF

PRIORITY

This application claims the benefit of priority to U.S. Provisional Patent Application No. 63/231,112, filed Aug. 9, 2021, which is incorporated by reference in its entirety into this application.

BACKGROUND

A guidewire is typically placed in a blood vessel with an introducer assembly before inserting a central venous catheter ("CVC") or the like into the blood vessel over the guidewire. The introducer assembly typically includes a needle connected to a syringe. Upon accessing the blood vessel with the needle, the needle must be disconnected from the syringe to allow insertion of the guidewire into the needle through a needle hub thereof and, subsequently, into the blood vessel. Disconnecting the needle from the syringe as well as inserting the guidewire into the needle risk puncturing a backwall of the blood vessel, losing access to the blood vessel, or both due to overhandling the needle. What is needed is an introducer assembly that does not require disconnecting the needle from the syringe for inserting the guidewire into the blood vessel.

Disclosed herein are introducer components, assemblies, and methods that address the foregoing.

SUMMARY

Disclosed herein is an introducer assembly including, in some embodiments, a syringe, a needle assembly fluidly connected to the syringe, and an access guidewire. The needle assembly includes a needle and an access guidewire-advancement mechanism. The needle includes a needle shaft and a needle hub. The needle shaft includes a sigmoid portion between a distal linear portion and a proximal linear portion as well as a port in a transition from the sigmoid portion of the needle shaft to the distal linear portion of the needle shaft. The needle hub is over the proximal linear portion of the needle shaft. The access guidewire-advancement mechanism is mounted on the proximal linear portion of the needle shaft distal of the needle hub. The access guidewire is loaded in both the access guidewire-advancement mechanism and a needle-shaft lumen in the distal linear portion of the needle shaft in a ready-to-deploy state of the introducer assembly.

In some embodiments, the access guidewire extends along a barrel wall of the syringe, through the access guidewire-advancement mechanism, through the port in the needle shaft, and into the needle-shaft lumen in the distal linear portion of the needle shaft without appreciably bending. A distal end of the access guidewire is disposed just proximal of a needle tip in the distal linear portion of the needle shaft in the ready-to-deploy state of the introducer assembly.

In some embodiments, the access guidewire includes a 'J'-shaped guidewire tip. The guidewire tip assumes a straightened state in the ready-to-deploy state of the introducer assembly. The guidewire tip also assumes a curved state when the guidewire tip is advanced beyond a distal end of the needle shaft in a deployed state of the introducer assembly.

In some embodiments, the access guidewire includes a bare-wire portion and a wound-wire portion proximal of the bare-wire portion. The bare-wire portion distally extends through the port in at least the ready-to-deploy state of the introducer assembly.

In some embodiments, the access guidewire includes a proximal portion proximally extending from the access guidewire-advancement mechanism in the ready-to-deploy state of the introducer assembly. The proximal portion of the access guidewire is disposed in a sterile barrier configured to maintain sterility of the access guidewire.

In some embodiments, the port includes a valve configured to form a fluid-tight seal around the access guidewire.

In some embodiments, the valve includes a split septum compressed in the port.

In some embodiments, the access guidewire-advancement mechanism includes a thumbwheel device. The thumbwheel device is configured to advance the access guidewire when the access guidewire is pressed into a thumbwheel and the thumbwheel is rotated.

In some embodiments, the needle hub further includes a needle-hub connector. The needle-hub connector includes a needle-hub bore in a proximal portion of the needle hub. A syringe tip of the syringe is disposed in the needle-hub bore, thereby fluidly connecting the needle to the syringe.

Also disclosed herein is a needle assembly including, in some embodiments, a needling having a needle shaft and a needle hub over the needle shaft. The needle shaft includes a sigmoid portion between a distal linear portion and a proximal linear portion as well as a port in a transition from the sigmoid portion of the needle shaft to the distal linear portion of the needle shaft. The needle hub is over the proximal linear portion of the needle shaft.

In some embodiments, the needle assembly further includes an access guidewire-advancement mechanism. The access guidewire-advancement mechanism is over the proximal linear portion of the needle shaft distal of the needle hub.

In some embodiments, the port includes a valve configured to form a fluid-tight seal around an access guidewire.

In some embodiments, the valve includes a split septum compressed in the port.

In some embodiments, the access guidewire-advancement mechanism includes a thumbwheel device. The thumbwheel device is configured to advance an access guidewire when the access guidewire is pressed into a thumbwheel and the thumbwheel is rotated.

Also disclosed herein is a method for securing vascular access. The method includes, in some embodiments, an introducer assembly-obtaining step, a needle tract-establishing step, and an access guidewire-advancing step. The introducer assembly-obtaining step includes obtaining an introducer assembly. The introducer assembly includes a syringe and a needle assembly fluidly connected to the syringe. The needle assembly includes a needle and an access guidewire-advancement mechanism. The needle includes a sigmoid portion between a distal linear portion and a proximal linear portion with a port in a transition from the sigmoid portion of the needle shaft to the distal linear portion of the needle shaft. The access guidewire-advancement mechanism is mounted on the proximal linear portion of the needle shaft distal of the needle hub for advancing an access guidewire into a blood-vessel lumen of a patient. The needle tract-establishing step includes establishing a needle tract from an area of skin to the blood-vessel lumen with the needle. The access guidewire-advancing step includes advancing at least a guidewire tip of the access guidewire into the blood-vessel lumen for the securing of the vascular access.

In some embodiments, the method further includes an introducer assembly-adjusting step. The introducer assembly-adjusting step includes adjusting the introducer assembly such that the introducer assembly is in a ready-to-deploy state thereof. In the ready-to-deploy state of the introducer assembly, the guidewire tip of the access guidewire is disposed just proximal of a needle tip in the distal linear portion of the needle shaft for performing the access guidewire-advancing step immediately upon the establishing of the needle tract in the needle tract-establishing step.

In some embodiments, the access guidewire extends along a barrel wall of the syringe, through the access guidewire-advancement mechanism, through the port in the needle shaft, and into a needle-shaft lumen in the distal linear portion of the needle shaft without appreciably bending in the ready-to-deploy state of the introducer assembly.

In some embodiments, the access guidewire-advancing step includes rotating a thumbwheel of the access guidewire-advancement mechanism while the access guidewire is pressed against the thumbwheel.

In some embodiments, the access guidewire-advancing step allows the guidewire tip of the access guidewire to transition from a straightened state in the needle shaft to a curved state in the blood-vessel lumen.

In some embodiments, the method further includes a plunger-withdrawing step. The plunger-withdrawing step includes withdrawing a plunger from a barrel of the syringe to create a slight vacuum before reaching the blood-vessel lumen in the needle tract-establishing step. The slight vacuum ensures blood flashes back into at least a syringe tip to confirm the establishing of the needle tract.

In some embodiments, the method further includes a blood-aspirating step. The blood-aspirating step includes aspirating blood with the syringe to confirm the establishing of the needle tract. A valve disposed in the port is configured to form a fluid-tight seal around a bare-wire portion of the access guidewire for maintaining a vacuum during the blood-aspirating step.

In some embodiments, the method further includes a needle-withdrawing step. The needle-withdrawing step includes withdrawing the needle from the patient leaving the access guidewire in the blood-vessel lumen.

In some embodiments, the needle-withdrawing step includes holding the access guidewire in place at or near the area of skin including the needle tract while withdrawing the needle over a proximal portion of the access guidewire in the needle-withdrawing step.

In some embodiments, the method further includes a syringe-and-needle disconnecting step. The syringe-and-needle disconnecting step includes disconnecting the needle from the syringe before performing the needle-withdrawing step.

In some embodiments, the method further includes an air-bleeding step. The air-bleeding step includes bleeding air into the port while performing the needle-withdrawing step by pushing the access guidewire to a side of the port. The bleeding of the air into the port obviates disconnecting the needle from the syringe.

These and other features of the concepts provided herein will become more apparent to those of skill in the art in view of the accompanying drawings and following description, which describe particular embodiments of such concepts in greater detail.

DRAWINGS

DESCRIPTION

Figure 1:
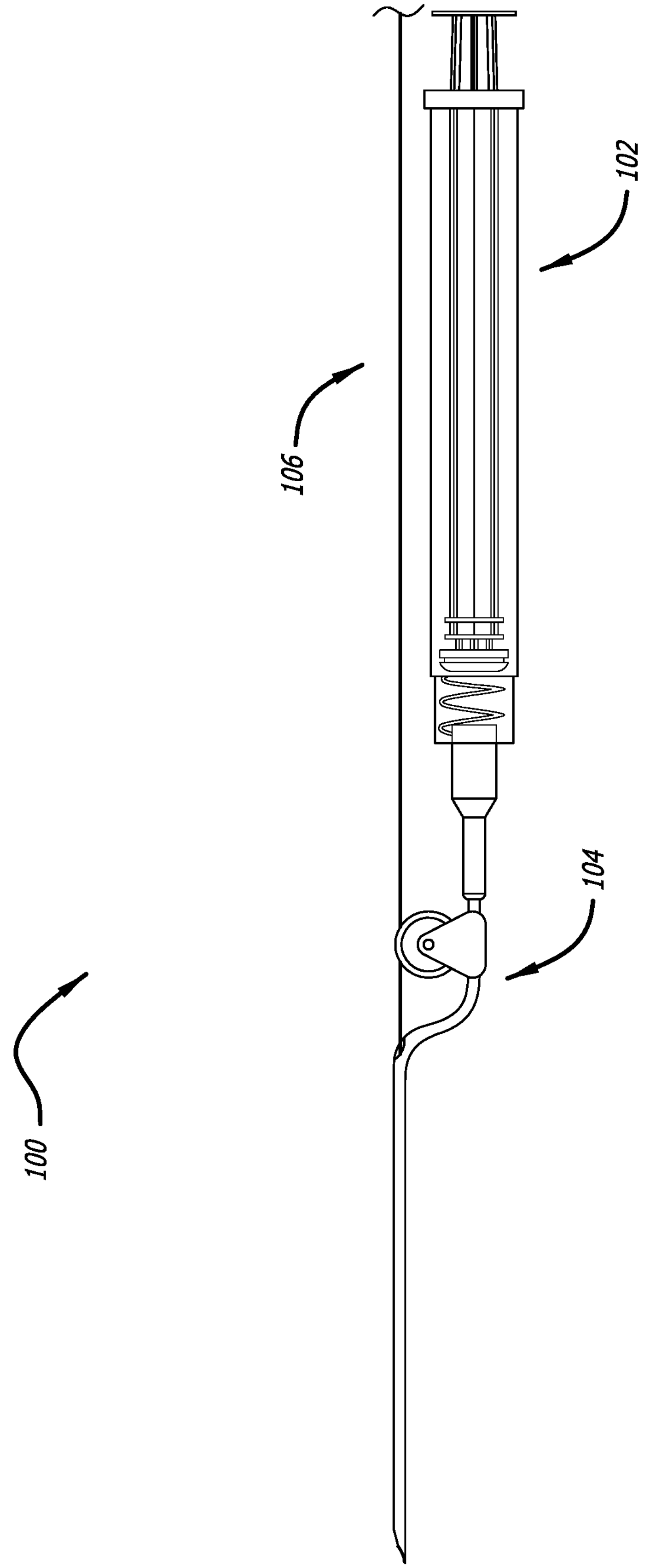
FIG. 1 illustrates a side view of an introducer assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, a guidewire is typically placed in a blood vessel with an introducer assembly before inserting a CVC or the like into the blood vessel over the guidewire. The introducer assembly typically includes a needle connected to a syringe. Upon accessing the blood vessel with the needle, the needle must be disconnected from the syringe to allow insertion of the guidewire into the needle through a needle hub thereof and, subsequently, into the blood vessel. Disconnecting the needle from the syringe as well as inserting the guidewire into the needle risk puncturing a backwall of the blood vessel, losing access to the blood vessel, or both due to overhandling the needle. What is needed is an introducer assembly that does not require disconnecting the needle from the syringe for inserting the guidewire into the blood vessel.

Disclosed herein are introducer components, assemblies, and methods that do not require disconnecting the needle from the syringe for inserting the guidewire into a blood vessel like typical introducer assemblies. Such introducer components, assemblies, and methods are advantageous in that they do not have the same risk of puncturing a backwall of the blood vessel or losing access to the blood vessel due to overhandling. In an example, an introducer assembly is disclosed including a syringe and a needle assembly fluidly connected thereto. The needle assembly can include a needle and an access guidewire-advancement mechanism mounted on a proximal linear portion of a needle shaft of the needle. The needle shaft can include a sigmoid portion between a distal linear portion of the needle shaft and the proximal linear portion as well as a port in a transition from the sigmoid portion to the distal linear portion of the needle shaft. An access guidewire can be loaded in both the access guidewire-advancement mechanism and a needle-shaft lumen in the distal linear portion of the needle shaft in a ready-to-deploy state of the introducer assembly. In another example, a method is disclosed for securing vascular access with the foregoing introducer assembly. Again, these and other features will become more apparent in view of the accompanying drawings and following description, which describe particular embodiments in greater detail.

Introducer Assemblies

Figure 2:
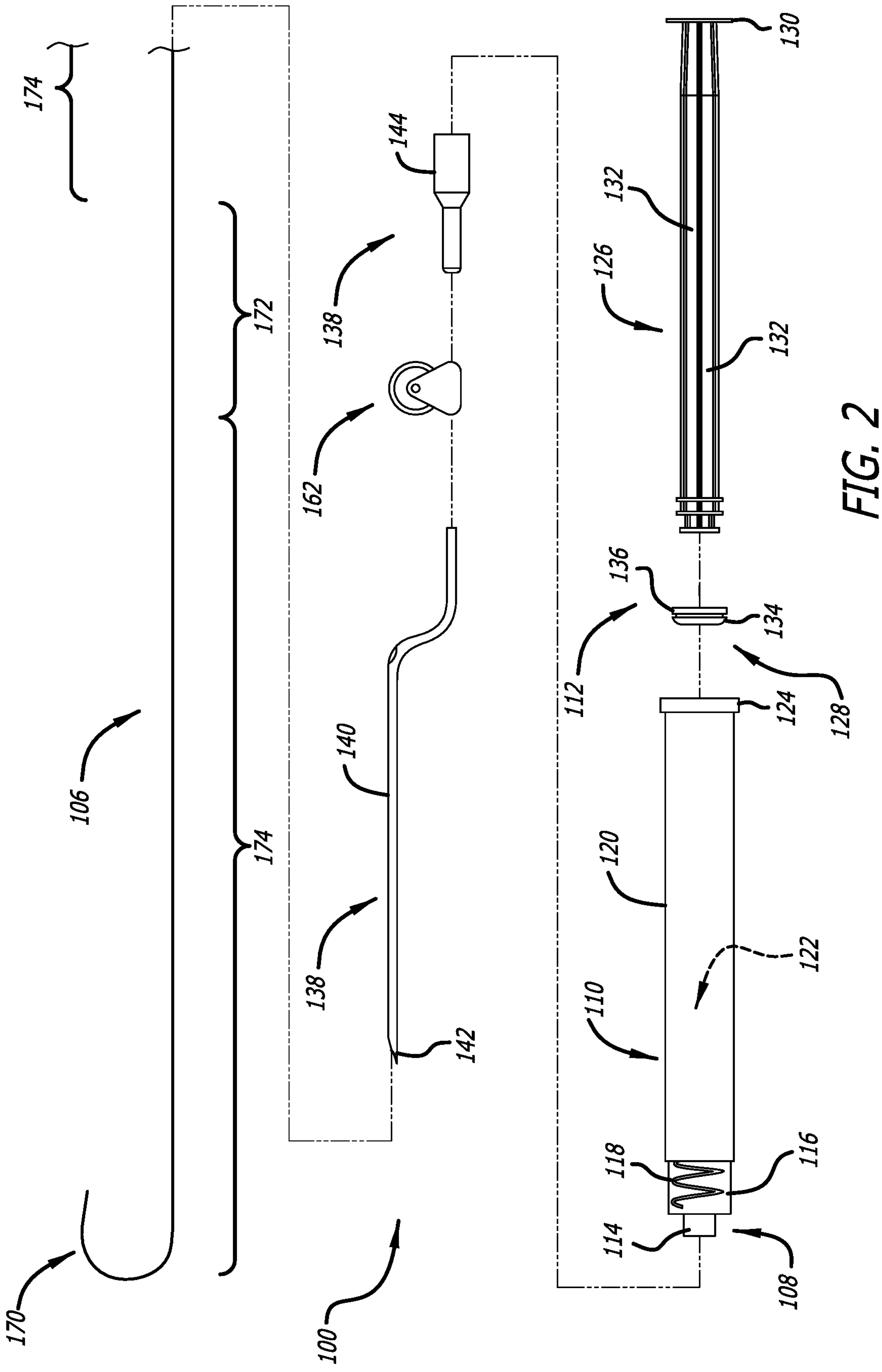
FIG. 2 illustrates an exploded view of an introducer assembly in accordance with some embodiments.

FIGS. 1 and 2 illustrate various views of an introducer assembly 100 in accordance with some embodiments.

As shown, the introducer assembly 100 includes a syringe 102 and a needle assembly 104 fluidly connected to the syringe 102 in at least a ready-to-deploy state of the introducer assembly 100. In addition, the introducer assembly 100 can include an access guidewire 106 slidably disposed in the introducer assembly 100 in the ready-to-deploy state of the introducer assembly 100. Indeed, as set forth in more detail below, the access guidewire 106 is loaded in both the access guidewire-advancement mechanism (e.g., the thumbwheel device 162) and the needle-shaft lumen 150 in the distal linear portion 152 of the needle shaft 140 in the ready-to-deploy state of the introducer assembly 100. Loaded as such in the introducer assembly 100, the access guidewire 106 extends along the barrel wall 120 of the syringe 102, through or over the access guidewire-advancement mechanism, through the port 148 in the needle shaft 140, and into the needle-shaft lumen 150 in the distal linear portion 152 of the needle shaft 140 just proximal of the needle tip 142, notably, without appreciably bending. In this way, the access guidewire 106 is available to be immediately and directly advanced into a blood-vessel lumen of a patient upon establishing a needle tract thereto with the needle 138.

The syringe 102 includes a syringe hub 108, a barrel 110, and a plunger 112 disposed in the barrel 110 in at least the ready-to-deploy state of the introducer assembly 100.

The syringe hub 108 includes a syringe tip 114 extending from a distal portion (e.g., a distal end) of the barrel 110. In addition, the syringe hub 108 can include a threaded collar 116 extending from the distal portion (e.g., the distal end) of the barrel 110 around the syringe tip 114.

The syringe tip 114 is configured to insert into the needle-hub bore 160 of the needle hub 144 for fluidly connecting the syringe 102 to the needle 138. Indeed, the syringe tip 114 can have a Luer taper (e.g., a 6% taper) configured to insert into the needle-hub bore 160, which needle-hub bore 160 is complementarily configured as set forth below.

The threaded collar 116 includes internal threads 118 configured to screw together with the optional needle-hub flange of the needle hub 144 set forth below. When present, the threaded collar 116 of the syringe hub 108 advantageously provides a so-called Luer lock-style connection with the needle-hub flange of the needle hub 144 for added security against inadvertent disconnection over that provided by an otherwise Luer slip-style connection.

The barrel 110 includes a barrel wall 120, a barrel chamber 122 defined by the barrel wall 120, and a barrel flange 124, barrel collar, or the like outwardly extending from a proximal portion (e.g., a proximal end) of the barrel 110 or barrel wall 120 configured for actuating the syringe 102 together with the plunger flange 130, the plunger collar, or the like set forth below.

The barrel chamber 122 is configured to accept the plunger 112 when inserted therein. Indeed, the barrel chamber 122 extends from a distal end of the barrel 110, which is a closed end of the barrel 110 (excepting the syringe tip 114), to the proximal end of the barrel 110, which is an open end of the barrel 110 into which the plunger 112 can be inserted.

The plunger 112 includes a one-piece plunger shaft 126, a piston 128 fitted over a distal portion (e.g., a distal end) of the plunger shaft 126, and a plunger flange 130, a plunger collar, or the like outwardly extending from a proximal portion (e.g., a proximal end) of the plunger 112 configured for actuating the syringe 102 together with the barrel flange 124, barrel collar, or the like.

The plunger shaft 126 can include orthogonal struts 132 meeting along their longitudinal edges at a central axis of the plunger shaft 126. However, the plunger shaft 126 can take other forms, so the plunger shaft 126 is not limited to the orthogonal struts 132.

The piston 128, which can be an integral, elastomeric piston, includes one or more rings configured to respectively form one or more seals with the barrel wall 120. The one-or-more rings include at least a leading ring 134 configured to form a seal with the barrel wall 120. The one-or-more rings can also include a trailing ring 136 as shown in FIG. 2. Like the leading ring 134, the trailing ring 136 is configured to form a seal with the barrel wall 120. Indeed, the trailing ring 136, when present, provides a backup seal with the barrel wall 120. Together, the leading ring 134 and the trailing ring 136 ensure the seal (e.g., the seal provided by the leading ring 134, the trailing ring 136, or both the leading ring 134 and the trailing ring 136) between the piston 128 and the barrel wall 120 remains intact while the syringe 102 is actuated, thereby allowing the syringe 102 to consistently aspirate a liquid such as blood when the plunger 112 is withdrawn from the barrel 110.

Figure 3:
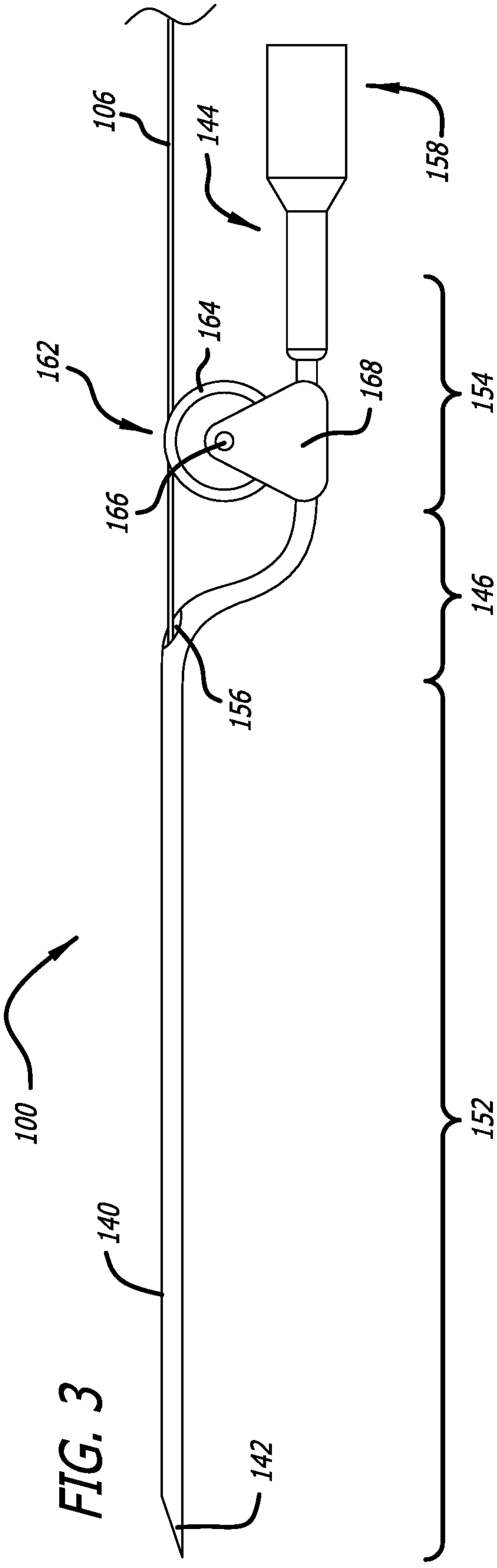
FIG. 3 illustrates a detailed view of a needle assembly of the introducer assembly in accordance with some embodiments.
Figure 4:
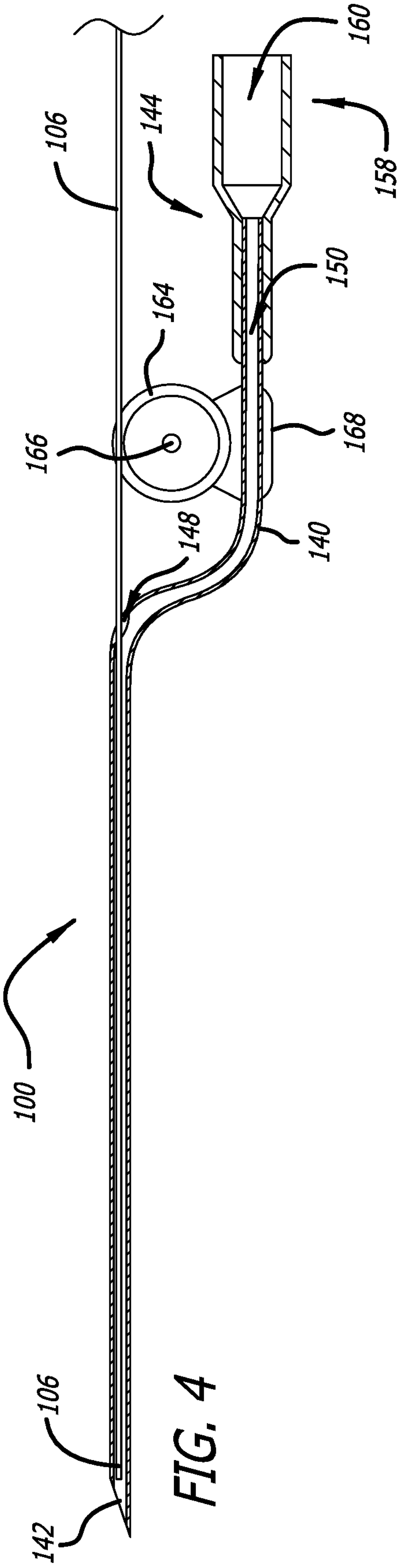
FIG. 4 illustrates a longitudinal cross section of the needle assembly in accordance with some embodiments.

FIGS. 3 and 4 illustrate various views of the needle assembly 104 in accordance with some embodiments.

The needle assembly 104 includes a needle 138 and an access guidewire-advancement mechanism such as the thumbwheel device 162 set forth below.

The needle 138 includes a needle shaft 140, a needle tip 142 in a distal linear portion 152 of the needle shaft 140, and a needle hub 144 over the proximal linear portion 154 of the needle shaft 140 set forth below.

The needle shaft 140 includes a sigmoid portion 146, a port 148, and a needle-shaft lumen 150 extending from an opening in the needle tip 142 to a proximal end of the needle shaft 140.

The sigmoid portion 146 of the needle shaft 140 is between a distal linear portion 152 of the needle shaft 140 and a proximal linear portion 154 of the needle shaft 140. The sigmoid portion 146 is configured to offset a central axis of the syringe 102 from that of the distal linear portion 152 of the needle shaft 140 such that the access guidewire 106 can extend along the barrel wall 120 of the syringe 102, through or over the access guidewire-advancement mechanism (e.g., the thumbwheel device 162 set forth below), through the port 148 in the needle shaft 140, and into the needle-shaft lumen 150 in the distal linear portion 152 of the needle shaft 140 without appreciably bending. In this way, the access guidewire 106 is available to be directly advanced into a blood-vessel lumen of a patient upon establishing a needle tract thereto with the needle 138.

The port 148 is in the sigmoid portion 146 of the needle shaft 140 or a transition from the sigmoid portion 146 to the distal linear portion 152. The port 148 includes a valve 156, which can be a septum or split septum disposed in the port 148. The valve 156 is configured to form a fluid-tight seal around the access guidewire 106 (e.g., the bare-wire portion 172 of the access guidewire 106) when passed through the port 148 and into the needle-shaft lumen 150 of the needle shaft 140.

The needle hub 144 includes a needle-hub connector 158 in a proximal portion of the needle hub 144. The needle-hub connector 158, in turn, includes a needle-hub bore 160 and an optional needle-hub flange about the needle-hub connector 158.

The needle-hub bore 160 is configured to accept the syringe tip 114 therein for fluidly connecting the needle 138 to the syringe 102. Indeed, the needle-hub bore 160 can have a Luer taper (e.g., a 6% taper) configured to accept the syringe tip 114 therein, which syringe tip 114 is complementarily configured as set forth above.

While not shown, the optional needle-hub flange is configured to screw together with the internal threads 118 of the threaded collar 116 of the syringe hub 108. When present, the needle-hub flange advantageously provides a so-called Luer lock-style connection with the internal threads 118 of the threaded collar 116 of the syringe hub 108 for added security against inadvertent disconnection over that provided by an otherwise Luer slip-style connection.

The access guidewire-advancement mechanism can include, but is not limited to, a thumbwheel device 162. The thumbwheel device 162 can include a thumbwheel 164 mounted on an axle 166 between arms of a thumbwheel chassis 168, which, in turn, is mounted on the proximal linear portion 154 of the needle shaft 140 distal of the needle hub 144. Such a thumbwheel device 162 is configured to advance the access guidewire 106 when the access guidewire 106 is pressed into the thumbwheel 164 and the thumbwheel 164 is rotated.

Again, the introducer assembly 100 can include the access guidewire 106 slidably disposed in the introducer assembly 100 in the ready-to-deploy state of the introducer assembly 100. Indeed, the access guidewire 106 is loaded in both the access guidewire-advancement mechanism (e.g., the thumbwheel device 162) and the needle-shaft lumen 150 in the distal linear portion 152 of the needle shaft 140 in the ready-to-deploy state of the introducer assembly 100. Loaded as such in the introducer assembly 100, the access guidewire 106 extends along the barrel wall 120 of the syringe 102, through or over the access guidewire-advancement mechanism, through the port 148 or the valve 156 thereof in the needle shaft 140, and into the needle-shaft lumen 150 in the distal linear portion 152 of the needle shaft 140 just proximal of the needle tip 142, notably, without appreciably bending. In this way, the access guidewire 106 is available to be immediately and directly advanced into a blood-vessel lumen of a patient upon establishing a needle tract thereto with the needle 138.

The access guidewire 106 can include a guidewire tip 170 in the form of a 'J'-shaped guidewire tip configured to prevent puncturing a back wall of a blood vessel. Such a guidewire tip assumes a straightened state in the ready-to-deploy state of the introducer assembly 100 and a curved state when the guidewire tip 170 is advanced beyond the needle tip 142 in a deployed state of the introducer assembly 100.

The access guidewire 106 can further include a bare-wire portion 172 and a wound-wire portion 174 distal of the bare-wire portion 172, proximal of the bare-wire portion 172, or both. The bare-wire portion 172 distally extends through the port 148 or the valve 156 thereof in at least the ready-to-deploy state of the introducer assembly 100 for forming the fluid-tight seal. Indeed, to maintain the fluid-tight seal even when a distal portion of the access guidewire 106 is advanced into a blood-vessel lumen, the bare-wire portion 172 can further distally extend through the port 148 or the valve 156 thereof in one-or-more deployed states of the introducer assembly 100 as well. Notably, the access guidewire 106 need not have the bare-wire portion 172 and the wound-wire portion 174. At least the foregoing bare-wire portion 172 can instead be a flat-wound or ground-wound portion of the access guidewire 106, wherein the flat-wound portion includes windings of a tape instead of a round wire, and wherein the ground-wound portion includes windings of a round wire ground down to flatten the windings.

Notably, the access guidewire 106 includes a proximal portion proximally extending from the access guidewire-advancement mechanism (e.g., the thumbwheel device 162) in the ready-to-deploy state of the introducer assembly 100. While not shown, the proximal portion of the access guidewire 106 can be disposed in a sterile barrier such as an elongate bag or even a guidewire-dispensing device, the sterile barrier or guidewire-dispensing device configured to maintain sterility of the access guidewire 106.

Methods

Methods include at least a method for securing vascular access. Such a method includes one or more steps selected from an introducer assembly-obtaining step, an introducer assembly-adjusting step, a needle tract-establishing step, a plunger-withdrawing step, a blood-aspirating step, an access guidewire-advancing step, a syringe-and-needle disconnecting step, an air-bleeding step, and a needle-withdrawing step.

The introducer assembly-obtaining step includes obtaining the introducer assembly 100. As set forth above, the introducer assembly 100 includes the syringe 102 and the needle assembly 104 fluidly connected to the syringe 102. The needle assembly 104 includes the needle 138 and the access guidewire-advancement mechanism (e.g., the thumbwheel device 162). The needle 138 includes the sigmoid portion 146 between the distal linear portion 152 and the proximal linear portion 154 with the port 148 in the transition from the sigmoid portion 146 of the needle shaft 140 to the distal linear portion 152 of the needle shaft 140. The access guidewire-advancement mechanism is mounted on the proximal linear portion 154 of the needle shaft 140 distal of the needle hub 144 for advancing the access guidewire 106 into a blood-vessel lumen of a patient.

The introducer assembly-adjusting step includes adjusting the introducer assembly 100 such that the introducer assembly 100 is in the ready-to-deploy state thereof if not already upon performing the introducer assembly-obtaining step. Again, in the ready-to-deploy state of the introducer assembly 100, the guidewire tip 170 of the access guidewire 106 is just proximal of the needle tip 142 in the distal linear portion 152 of the needle shaft 140 for performing the access guidewire-advancing step immediately upon the establishing of the needle tract in the needle tract-establishing step. A remainder of the access guidewire 106 extends along the barrel wall 120 of the syringe 102, through or over the access guidewire-advancement mechanism (e.g., the thumbwheel device 162), through the port 148 in the needle shaft 140, and into the needle-shaft lumen 150 in the distal linear portion 152 of the needle shaft 140 without appreciably bending of the access guidewire 106.

The needle tract-establishing step includes establishing a needle tract from an area of skin to a blood-vessel lumen of a patient with the needle 138.

The plunger-withdrawing step includes withdrawing the plunger 112 from the barrel 110 of the syringe 102 to create a slight vacuum before reaching the blood-vessel lumen in the needle tract-establishing step. The slight vacuum ensures blood flashes back into at least the syringe tip 114 to confirm the establishing of the needle tract in the needle tract-establishing step.

The blood-aspirating step includes aspirating blood with the syringe 102 to confirm the establishing of the needle tract in the needle tract-establishing step. The valve 156 disposed in the port 148 is configured to form a fluid-tight seal around the bare-wire portion 172 of the access guidewire 106 for maintaining a vacuum during the blood-aspirating step.

Figure 5:
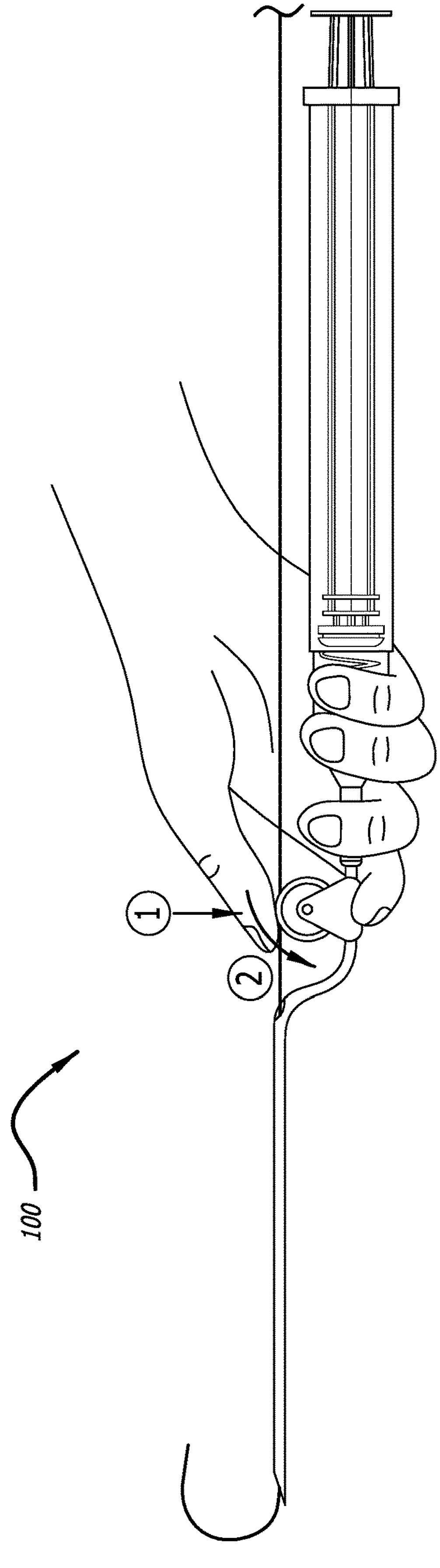
FIG. 5 illustrates a portion of a method of the introducer assembly in accordance with some embodiments.

FIG. 5 illustrates the access guidewire-advancing step of the method in accordance with some embodiments.

The access guidewire-advancing step includes rotating the thumbwheel 164 of the thumbwheel device 162 as the access guidewire-advancement mechanism while the access guidewire 106 is pressed against the thumbwheel 164 to advance at least the guidewire tip 170 of the access guidewire 106 into the blood-vessel lumen for the securing of the vascular access. The access guidewire-advancing step allows the guidewire tip 170 of the access guidewire 106 to transition from the straightened state in the needle-shaft lumen 150 of the needle shaft 140 to the curved state in the blood-vessel lumen.

The syringe-and-needle disconnecting step includes disconnecting the needle 138 from the syringe 102 before performing the needle-withdrawing step. However, the syringe-and-needle disconnecting step need not be performed if the air-bleeding step is performed.

The needle-withdrawing step includes withdrawing the needle 138 from the patient leaving the access guidewire 106 in the blood-vessel lumen. The needle-withdrawing step can include holding the access guidewire 106 in place at or near the area of skin including the needle tract while withdrawing the needle 138 over the proximal portion of the access guidewire 106.

The air-bleeding step includes bleeding air into the port 148 while performing the needle-withdrawing step by pushing the access guidewire 106 to a side of the port 148 against the valve 156; however, in some embodiments, the needle hub 144 includes a push-button bleed valve on another side of the needle hub 144 for the air-bleeding step. The bleeding of air into the port 148 obviates the disconnecting step of disconnecting the needle 138 from the syringe 102. That said, both the syringe-and-needle disconnecting step and the air-bleeding step can be performed in some embodiments.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. An introducer assembly, comprising:
- a syringe;
- a needle assembly fluidly connected to the syringe, the needle assembly including:
  - a needle including:
    - a needle shaft including:
      - a sigmoid portion between a distal linear portion and a proximal linear portion; and
      - a port in a transition from the sigmoid portion of the needle shaft to the distal linear portion of the needle shaft; and
    - a needle hub over the proximal linear portion of the needle shaft; and
  - an access guidewire-advancement mechanism mounted on the proximal linear portion of the needle shaft distal of the needle hub; and
- an access guidewire loaded in both the access guidewire-advancement mechanism and a needle-shaft lumen in the distal linear portion of the needle shaft in a ready-to-deploy state of the introducer assembly.

2. The introducer assembly of claim 1, wherein the access guidewire extends along a barrel wall of the syringe, through the access guidewire-advancement mechanism, through the port in the needle shaft, and into the needle-shaft lumen in the distal linear portion of the needle shaft without appreciably bending, a distal end of the access guidewire disposed just proximal of a needle tip in the distal linear portion of the needle shaft in the ready-to-deploy state of the introducer assembly.

3. The introducer assembly of claim 1, wherein the access guidewire includes a 'J'-shaped guidewire tip that assumes a straightened state in the ready-to-deploy state of the introducer assembly and a curved state when the 'J'-shaped guidewire tip is advanced beyond a distal end of the needle shaft in a deployed state of the introducer assembly.

4. The introducer assembly of claim 1, wherein the access guidewire includes a bare-wire portion and a wound-wire portion proximal of the bare-wire portion, the bare-wire portion distally extending through the port in at least the ready-to-deploy state of the introducer assembly.

5. The introducer assembly of claim 1, wherein the access guidewire includes a proximal portion proximally extending from the access guidewire-advancement mechanism in the ready-to-deploy state of the introducer assembly, the proximal portion of the access guidewire disposed in a sterile barrier configured to maintain sterility of the access guidewire.

6. The introducer assembly of claim 1, wherein the port includes a valve configured to form a fluid-tight seal around the access guidewire.

7. The introducer assembly of claim 6, wherein the valve includes a split septum compressed in the port.

8. The introducer assembly of claim 1, wherein the access guidewire-advancement mechanism includes a thumbwheel device configured to advance the access guidewire when the access guidewire is pressed into a thumbwheel and the thumbwheel is rotated.

9. The introducer assembly of claim 1, wherein the needle hub further includes a needle-hub connector including a needle-hub bore in a proximal portion of the needle hub, a syringe tip of the syringe disposed in the needle-hub bore, thereby fluidly connecting the needle to the syringe.

10. A needle assembly, comprising:
- a needle including:
  - a needle shaft including:
    - a sigmoid portion between a distal linear portion and a proximal linear portion; and
    - a port in a transition from the sigmoid portion of the needle shaft to the distal linear portion of the needle shaft, wherein the port includes a valve configured to form a fluid-tight seal around an access guidewire; and
  - a needle hub over the proximal linear portion of the needle shaft.

11. The needle assembly of claim 10, further comprising an access guidewire-advancement mechanism over the proximal linear portion of the needle shaft distal of the needle hub.

12. The needle assembly of claim 10, wherein the valve includes a split septum compressed in the port.

13. The needle assembly of claim 11, wherein the access guidewire-advancement mechanism includes a thumbwheel device configured to advance the access guidewire when the access guidewire is pressed into a thumbwheel and the thumbwheel is rotated.

14. A method for securing vascular access, comprising:
- obtaining an introducer assembly, the introducer assembly including:
  - a syringe; and
  - a needle assembly fluidly connected to the syringe, the needle assembly including:
    - a needle having a sigmoid portion between a distal linear portion and a proximal linear portion with a port in a transition from the sigmoid portion of a needle shaft to the distal linear portion of the needle shaft; and
    - an access guidewire-advancement mechanism mounted on the proximal linear portion of the needle shaft, distal of a needle hub for advancing an access guidewire into a blood-vessel lumen of a patient;
- establishing a needle tract from an area of skin to the blood-vessel lumen with the needle; and
- advancing at least a guidewire tip of the access guidewire into the blood-vessel lumen for securing the vascular access.

15. The method of claim 14, further comprising adjusting the introducer assembly such that the introducer assembly is in a ready-to-deploy state thereof with the guidewire tip of the access guidewire disposed just proximal of a needle tip in the distal linear portion of the needle shaft for advancing the access guidewire into the blood-vessel lumen immediately upon establishing the needle tract.

16. The method of claim 15, wherein the access guidewire extends along a barrel wall of the syringe, through the access guidewire-advancement mechanism, through the port in the needle shaft, and into a needle-shaft lumen in the distal linear portion of the needle shaft without appreciably bending in the ready-to-deploy state of the introducer assembly.

17. The method of claim 14, wherein advancing the access guidewire into the blood-vessel lumen includes rotating a thumbwheel of the access guidewire-advancement mechanism while the access guidewire is pressed against the thumbwheel.

18. The method of claim 14, wherein advancing the access guidewire into the blood-vessel lumen allows the guidewire tip of the access guidewire to transition from a straightened state in the needle shaft to a curved state in the blood-vessel lumen.

19. The method of claim 14, further comprising withdrawing a plunger from a barrel of the syringe to create a slight vacuum before reaching the blood-vessel lumen, the slight vacuum ensuring blood flashes back into at least a syringe tip to confirm establishing the needle tract.

20. The method of claim 14, further comprising aspirating blood with the syringe to confirm establishing the needle tract, a valve disposed in the port configured to form a fluid-tight seal around a bare-wire portion of the access guidewire for maintaining a vacuum during aspirating of the blood with the syringe.

21. The method of claim 14, further comprising withdrawing the needle from the patient leaving the access guidewire in the blood-vessel lumen.

22. The method of claim 21, wherein withdrawing the needle includes holding the access guidewire in place at or near the area of skin including the needle tract while withdrawing the needle over a proximal portion of the access guidewire.

23. The method of claim 21, further comprising disconnecting the needle from the syringe before withdrawing the needle from the patient.

24. The method of claim 21, further comprising bleeding air into the port while withdrawing the needle from the patient by pushing the access guidewire to a side of the port, the bleeding of air into the port obviating disconnecting the needle from the syringe.

* * * * *